(12) United States Patent
McLeish

(10) Patent No.: US 12,714,491 B2
(45) Date of Patent: Aug. 25, 2026

(54) SURGICAL ELECTRODE ASSEMBLY WITH FOCAL POINT PROJECTION

(71) Applicant: Arthrex, Inc., Naples, FL (US)

(72) Inventor: Eric D. McLeish, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 1078 days.

(21) Appl. No.: 17/863,766

(22) Filed: Jul. 13, 2022

(65) Prior Publication Data

US 2023/0014522 A1 Jan. 19, 2023

Related U.S. Application Data

(60) Provisional application No. 63/222,577, filed on Jul. 16, 2021.

(51) Int. Cl.
*A61B 18/14* (2006.01)
*A61B 18/00* (2006.01)

(52) U.S. Cl.
CPC .... *A61B 18/14* (2013.01); *A61B 2018/00577* (2013.01); *A61B 2018/142* (2013.01)

(58) Field of Classification Search
CPC ................ A61B 18/14; A61B 18/1492; A61B 2018/00577; A61B 2018/142; A61B 2018/00083; A61B 2018/126; A61B 2018/00738; A61B 2018/1405
See application file for complete search history.

(56) References Cited

U.S. PATENT DOCUMENTS

| | | | | |
|---|---|---|---|---|
| 5,281,213 | A | 1/1994 | Milder et al. | |
| 6,053,172 | A * | 4/2000 | Hovda | A61B 18/1482 606/41 |
| 6,120,499 | A * | 9/2000 | Dickens | A61B 18/1492 606/41 |
| 2001/0029368 | A1 | 10/2001 | Berube | |
| 2003/0014050 | A1 | 1/2003 | Sharkey et al. | |
| 2004/0193150 | A1 | 9/2004 | Sharkey et al. | |
| 2006/0271032 | A1 | 11/2006 | Chin et al. | |
| 2008/0234603 | A1* | 9/2008 | Bakos | A61B 18/14 600/567 |
| 2008/0312673 | A1 | 12/2008 | Viswanathan et al. | |
| 2009/0318914 | A1 | 12/2009 | Utley et al. | |

(Continued)

FOREIGN PATENT DOCUMENTS

| | | | |
|---|---|---|---|
| CA | 2118011 | C | 2/2000 |
| WO | 1995019738 | A1 | 7/1995 |

(Continued)

*Primary Examiner* — Joseph A Stoklosa
*Assistant Examiner* — Marina Delaney Templeton
(74) *Attorney, Agent, or Firm* — Price Heneveld LLP

(57) ABSTRACT

An electrode assembly for an electrosurgical ablator may include an insulator having a distal end portion and a proximal end portion. The insulator may include a rim forming a distal extent of the distal end portion and an aperture disposed in the distal end portion. An electrode is disposed in the aperture and forms a cavity having a profile shape recessed from the distal end portion toward the proximal end portion. The electrode assembly projects a focal point of an ablation region emitted from the supply electrode through the projecting rim to a projection distance beyond the distal extent.

23 Claims, 12 Drawing Sheets

(56) References Cited

U.S. PATENT DOCUMENTS

| | | | |
|---|---|---|---|
| 2010/0016854 A1 | 1/2010 | Carmel et al. | |
| 2018/0214202 A1* | 8/2018 | Howard | A61B 5/6852 |
| 2020/0360670 A1* | 11/2020 | Legum | A61B 18/1492 |
| 2021/0137592 A1 | 5/2021 | Viswanathan et al. | |
| 2022/0354567 A1* | 11/2022 | Melman | H04L 63/083 |

FOREIGN PATENT DOCUMENTS

| | | | |
|---|---|---|---|
| WO | 9636282 | A2 | 11/1996 |
| WO | 2008022148 | A2 | 2/2008 |
| WO | 201918672 | A1 | 10/2019 |

* cited by examiner

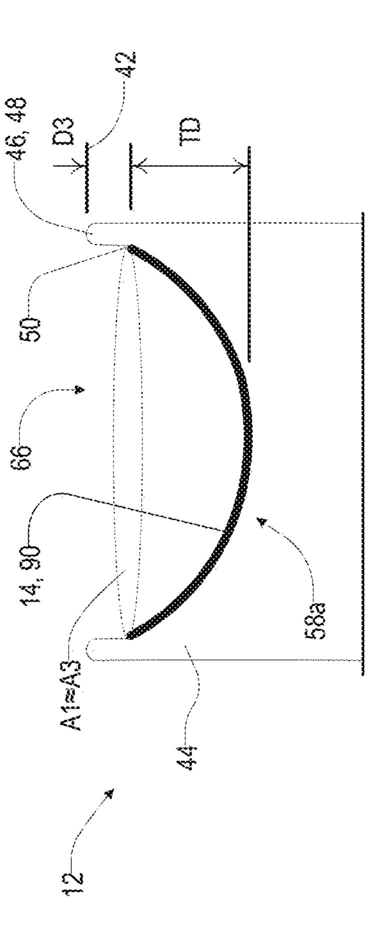
FIG. 7A
FIG. 7C
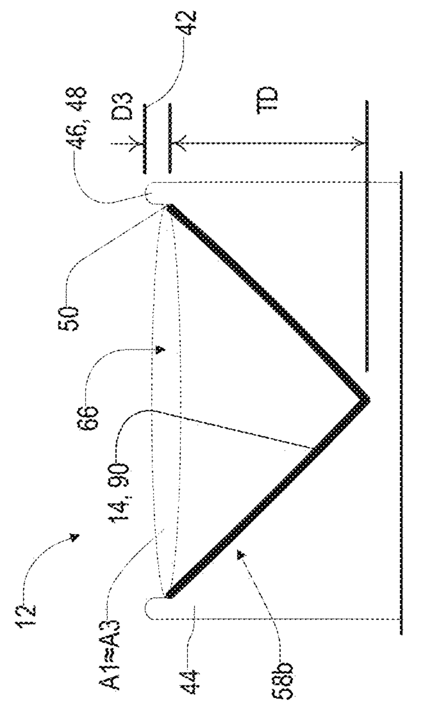
FIG. 7B

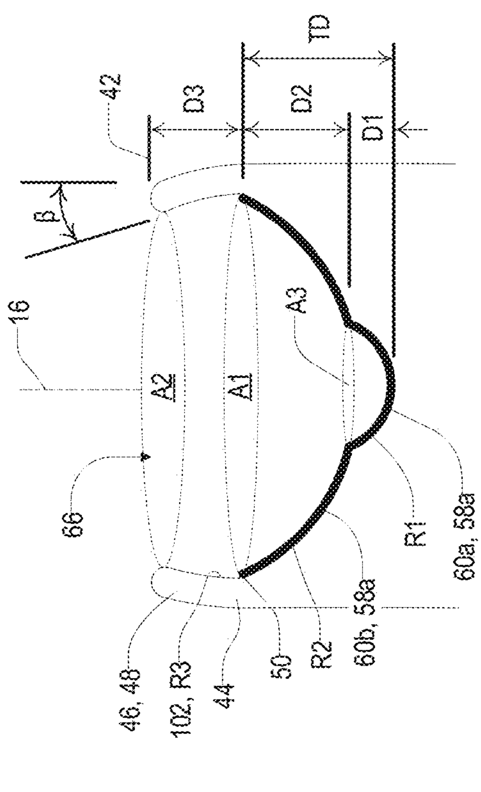
FIG. 8B
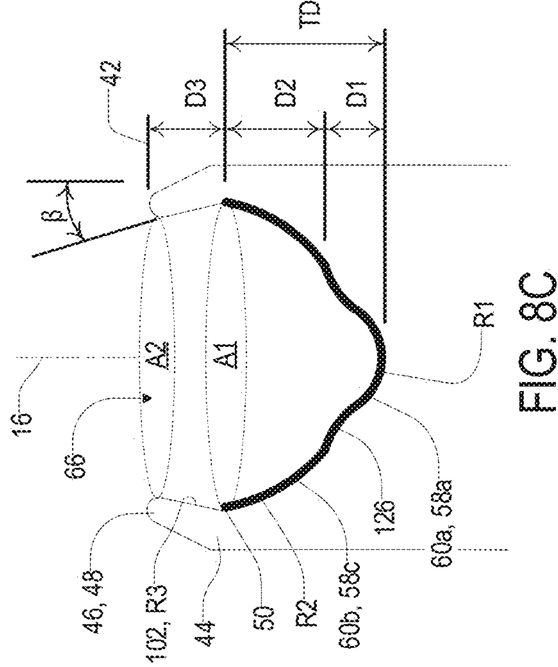
FIG. 8C
FIG. 8A

SURGICAL ELECTRODE ASSEMBLY WITH FOCAL POINT PROJECTION

CROSS-REFERENCE TO RELATED APPLICATIONS

This application claims priority under 35 U.S.C. § 119(e) and the benefit of U.S. Provisional Application No. 63/222,577 entitled SURGICAL ELECTRODE ASSEMBLY WITH FOCAL POINT PROJECTION, filed on Jul. 16, 2021, by Eric McLeish, the entire disclosure of which is incorporated herein by reference.

BACKGROUND

The present disclosure generally relates to an ablation device and, more particularly, to a system and electrode assembly for medical ablation procedures. In general, arthroscopic ablation devices may be used in medical procedures to remove or treat biological matter or tissue. Ablation procedures have a wide variety of applications and typically provide for minimally invasive surgical procedures to improve patient care.

SUMMARY

An ablation device may include a distal end portion with an electrode configured to generate an electric field immediately adjacent to the surface of the electrode. The electric field may be in the form of radio frequency (RF) energy that excites molecules in contact with the distal end portion, thereby generating heat to effectuate an ablation treatment. Accordingly, effective transmission of the energy emitted from the electrode may be achieved by placing the distal end portion of the ablation device in contact with the matter or tissue targeted for heating or treatment. Placing a probe tip or distal tip of an ablation device in contact with an area targeted for ablation treatment provides for the controlled application of the radio frequency (RF) energy of the electric field. However, in some cases, the proximity of the distal tip of the ablation device to the target region may result in an occluded view of the target region.

According to various aspects, the disclosure provides for an electrode assembly that may incorporate features to adjust a projected distance of a focal point of an ablation region generated by an ablation device. In general, the projected distance of the focal point may extend from an electrode of the electrode assembly beyond a distal end portion or extent of the electrode assembly. In this configuration, the RF energy transmitted from the electrode may be projected outward from the ablation device, such that tissue may be treated via the application of the RF energy without placing the ablation device in contact with the tissue. The structures and features of the electrode assembly may be combined in a variety of ways to adjust the projected distance of the focal point of the RF energy output from the electrode assembly. As discussed further in the following detailed description, variations to the structures, features, and their related geometry may be adjusted in coordination with the control signals communicated to the electrode assembly to adjust the projected distance to suit a variety of applications.

In some aspects, an electrode assembly for a surgical ablator is disclosed that may include an insulator comprising a distal end portion and a proximal end portion. The insulator may comprise a rim forming a distal extent of the distal end portion. The rim may form an aperture disposed in the distal end portion. A supply electrode may be disposed in the aperture and may form a cavity having a profile shape recessed from the distal end portion toward the proximal end portion. In operation, the electrode assembly may project a focal point of an ablation region emitted from the supply electrode through the aperture to a projection distance beyond the distal extent.

Additional aspects of the electrode assembly may include one or more of the following features:

- a projection axis that extends centrally from the supply electrode through the focal point and the profile shape forms an electrode angle relative to the projection axis, wherein the projection distance of the focal point may be a function of the electrode angle;
- the profile shape may extend along a varying slope that changes from a central portion of the supply electrode to a perimeter of the supply electrode;
- the electrode angle may be an average of the varying slope of the profile shape;
- the profile shape of the supply electrode may form a depth (D) of the aperture and the projection distance may extend to a distance of two times the depth (2D) from the distal end portion of the supply electrode;
- the rim may form an interior wall of the aperture that extends a first distance from the supply electrode to the distal extent;
- the first distance may be between 5% of the depth D (0.05D) to 100% of the depth D;
- the interior wall may define a cross section of the aperture formed by the rim;
- the cross section may decrease at an aperture angle along the first distance from the supply electrode to the distal extent;
- the cross section may decrease at an increasing rate along at least a portion of the first distance;
- the supply electrode may form a perimeter defining a first area and the aperture of the rim forms an opening proximate to the distal extent defining a second area;
- the first area may be greater than the second area;
- the focal point may be projected along a projection axis from a central portion of the supply electrode through the aperture of the rim to the projection distance;
- the profile shape of the cavity may extend from a perimeter of the supply electrode to a base of a central portion of the supply electrode over a depth ranging from 0.25 mm to 10 mm;
- the profile shape may comprise a rounded concave shape;
- the profile shape may comprise a conical shape;
- the profile shape may form an inner contour of the supply electrode having a first radius and an outer contour enclosing the inner contour having a second radius;
- the first radius may be smaller than the second radius; and/or
- a return electrode may be conductively separated from the supply electrode via the insulator and disposed adjacent to the proximal end portion.

In some aspects of the disclosure, a surgical ablation system may comprise an electrode assembly having a proximal end portion and a distal end portion. The electrode assembly may include an insulator comprising a rim a forming a distal extent of the distal end portion. The rim may form an aperture disposed in the distal end portion. A supply electrode may be disposed in the aperture and form a cavity having a profile shape recessed from the distal end portion toward the proximal end portion. In operation, the electrode assembly may project a focal point of an ablation region along a projection direction. The projection direction may extend from the supply electrode through the aperture of the rim to a projection distance beyond the distal extent. The system may further include a controller comprising a signal generator and a processor. The controller may be configured to control a radio frequency (RF) signal conducted to the supply electrode. The supply electrode may transmit RF energy to the focal point of the ablation region in response to the RF signal.

Additional aspects of the disclosure may include the ablation region defined perpendicular to the projection direction. The RF signal generated by the signal generator may be from approximately 200 W to 1000 W.

In some aspects of the disclosure, a surgical ablation apparatus may include an insulator comprising a proximal end portion and a distal end portion. The insulator may include a rim forming an aperture disposed in the distal end portion. A supply electrode may be disposed in the aperture and may form a cavity having a profile shape recessed from the distal end portion toward the proximal end portion. In operation, the supply electrode may project a focal point of an ablation region along a projection direction that extends from the supply electrode through the aperture of the rim to a projection distance beyond the distal end portion. At least one aspiration aperture may extend through the supply electrode to a lumen. The at least one aspiration aperture may be aligned with the focal point.

Additional aspects of the disclosure may include the at least one aspiration aperture corresponding to a plurality of aspiration apertures formed through the supply electrode. The plurality of aspiration apertures may be aligned with the focal point over the profile shape of the supply electrode.

These and other features, objects and advantages will become apparent upon reading the following description thereof together with reference to the accompanying drawings.

BRIEF DESCRIPTION OF THE DRAWINGS

FIG. 7A is a side cross-sectional view of an electrode assembly demonstrating a profile shape of a recessed portion of an active electrode;

FIG. 7B is a side cross-sectional view of an electrode assembly demonstrating a profile shape of a recessed portion of an active electrode;

FIG. 7C is a side cross-sectional view of an electrode assembly demonstrating a profile shape of a recessed portion of an active electrode;

FIG. 8A is a side cross-sectional view of an electrode assembly demonstrating a profile shape of a recessed portion of an active electrode;

FIG. 8B is a side cross-sectional view of an electrode assembly demonstrating a profile shape of a recessed portion of an active electrode;

FIG. 8C is a side cross-sectional view of an electrode assembly demonstrating a profile shape of a recessed portion of an active electrode;

DETAILED DESCRIPTION

Ablation devices and corresponding systems may provide beneficial utilities for minimally invasive medical procedures. Such procedures may limit patient recovery times and improve outcomes by applying minimally invasive surgical techniques and tools to access treated areas. As discussed in the following description, a distal end portion of an ablation device may include an electrode assembly configured to generate an electric field. The electric field may be in the form of RF energy that excites molecules local to the distal end portion, thereby generating heat to effectuate an ablation treatment. Accordingly, effective transmission of the energy emitted from the electrode may be achieved by placing the distal end portion of the ablation device in contact with the matter or tissue targeted for heating. The disclosure provides for a variety of features and assemblies for an electrode assembly, which may provide for the application of RF energy of the electric field over a projected distance extending beyond a distal extremity or tip portion of an ablation device. In this way, RF energy of the electric field may be applied to an ablation region that excites molecules at the projected distance to treat target regions of tissue without placing the ablation device in contact with tissue targeted for treatment.

Figure 1:
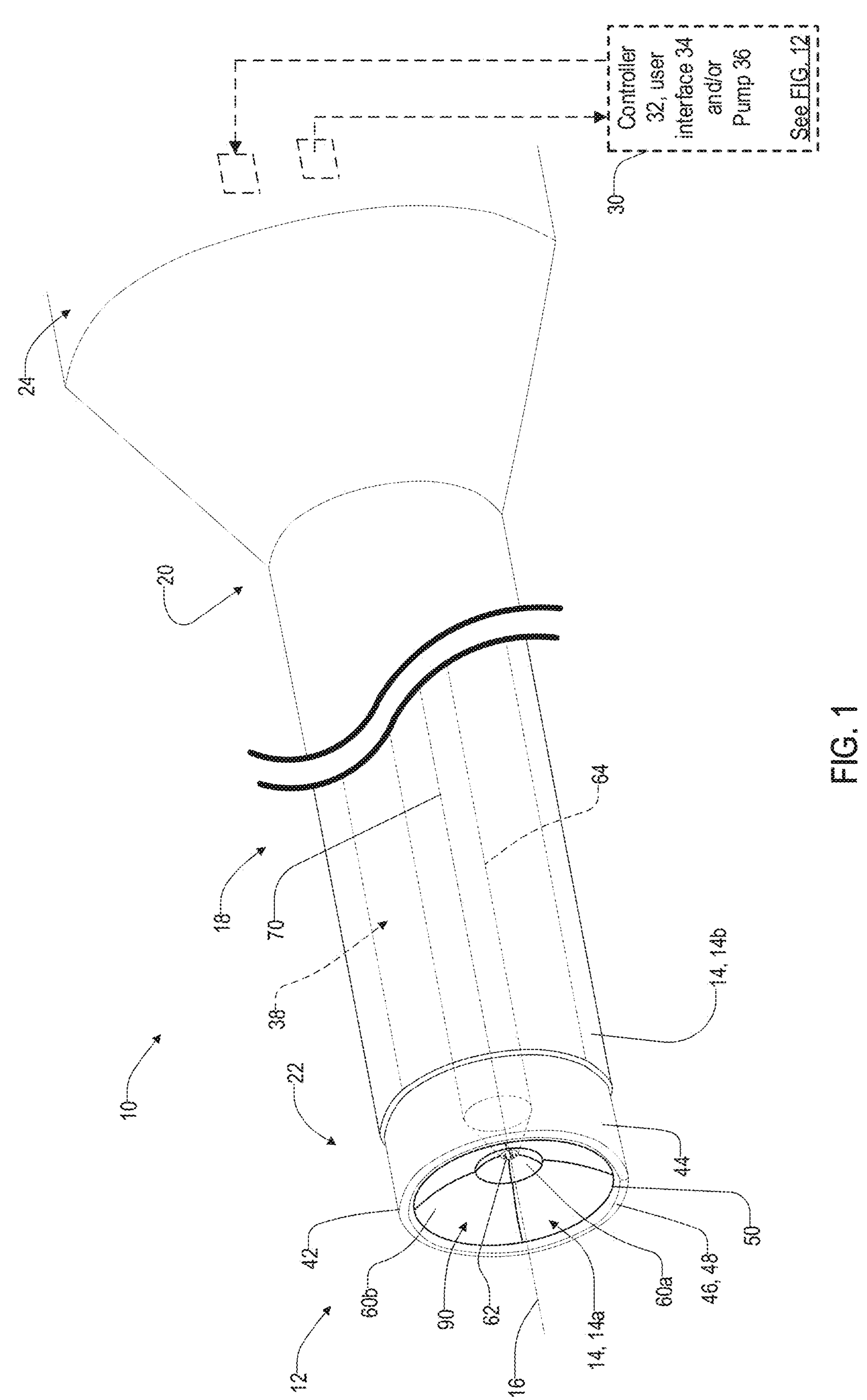
FIG. 1 is a projected view of an ablation device demonstrating an electrode assembly.
Figure 2:
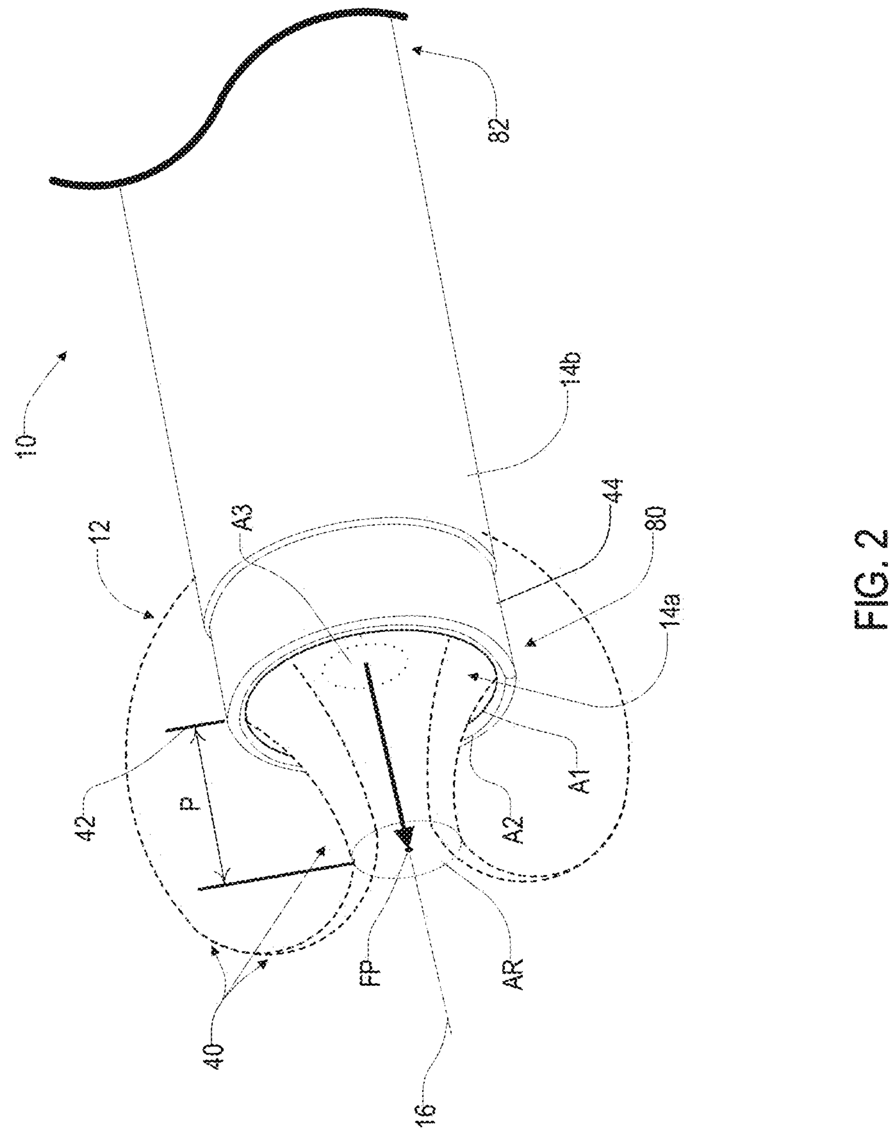
FIG. 2 is a projected view of an ablation device demonstrating an electric field transmitted from an active electrode to a focal point over a projected distance.

Referring to FIGS. 1 and 2, an ablation device 10 is shown demonstrating an exemplary embodiment of an electrode assembly 12 comprising a first electrode 14*a* and a second electrode 14*b*. The first electrode 14*a* may correspond to a supply electrode and is referred to as an active electrode 14*a* for clarity. The second electrode 14*b* may provide a return current path from the active electrode 14*a* and may be referred to as a return electrode 14*b*. As shown in FIG. 2, the electrode assembly 12 may be configured to project a focal point FP of an ablation region AR to a projected distance P. The projected distance P may be shifted or extended outward beyond an extent of the electrode assembly 12 and may extend from a central portion 60*a* of the active electrode 14*a* along a projection axis 16. Though discussed in reference to the projection axis 16, some geometries of the electrode assembly 12 may be asymmetrical, irregular, or elongated, such that the ablation region AR extends along a projection plane or surface rather than the linear projection axis 16.

In general, the ablation device 10 may be in the form a wand or catheter having an elongated body 18 extending from a proximal end portion 20 to a distal end portion 22. The electrode assembly 12 may be in connection with the distal end portion 22. Opposite the electrode assembly 12, the proximal end portion 20 may be in connection with a handle portion 24, which may include one or more interface devices configured to control the operation of an ablation system 30 via a controller 32 (see FIG. 12). In operation, control signals may be generated by the controller 32 and conducted to the active electrode 14*a* based on one or more settings, which may controlled via a user interface 34 comprising the interface devices. Further detailed discussion of the controller 32, the user interface, and a pump 36 or aspiration pump as they relate to the ablation system 30 is provided in reference to FIG. 12.

The electrode assembly 12 may be operably coupled to the controller 32 via one or more conductive connectors (not shown) that may pass through an interior passage 38 within the elongated body 18. The control signals from the controller 32 are communicated to the active electrode 14*a* and returned via the return electrode 14*b*. In this way, the electrode assembly 12 may generate an electric field 40 in response to receiving the control signals, which may be in the form of alternating current (AC) or RF signals. The oscillation of the control signals received by the electrode assembly 12 may generate an electric field 40 (e.g., an RF field) between the active electrode 14*a* or supply electrode and the return electrode 14*b* as depicted in FIG. 2. As provided in the following detailed examples, the novel structures of the electrode assembly 12 provide for the ablation region AR of the electric field 40 to be projected outward beyond a distal extent 42 of the electrode assembly 12 in response to an excitation resulting from the control signals. In this way, the electric field 40 may be generated, such that tissue may be effectively heated in the ablation region at the projected distance P. Put differently, the electrode assembly 12 may provide for the ablation device 10 to effectively heat tissue with the electric field 40 without requiring the ablation device 10 to come in contact with tissue targeted for treatment. By controlling the projected distance P beyond the distal extent 42 of the ablation device 10, the disclosure may provide for ablation treatment to be administered without the ablation device 10 contacting the tissue targeted for treatment or occluding a view of the tissue upon which the electric field 40 is acting.

An insulator 44 or insulating collar may separate the active electrode 14*a* from the return electrode 14*b*. In general, the insulator 44 may correspond to a non-conductive or electrically insulating structure that forms an insulating barrier between conductive materials of the electrodes 14. As demonstrated in the exemplary illustration, the insulator 44 forms a protruding lip 46 that may form a rim 48 that extends beyond a perimeter 50 of the active electrode 14*a*. The perimeter 50 of the active electrode 14*a* may correspond to a boundary between the conductive material of the active electrode 14*a* and insulating material of the insulator 44. In this configuration, the insulator 44 may extend beyond the active electrode 14*a* along the projection axis 16, and the distal extent 42 of the electrode assembly 12 may be defined by the proportions of the protruding lip 46. The insulator 44 may be of an electrically insulating material, such that the electric field 40 is induced rather than conducting the electrical charge directly from the active electrode 14*a* to the return electrode 14*b*. For example, the insulator 44 may be formed of a ceramic, silicone, glass, epoxy, or other non-electrically conductive materials. The electrodes 14 may be of conductive materials including metals and metal alloys, for example, stainless steel and stainless steel alloys, platinum and platinum alloys, gold and gold alloys, nickel and nickel alloys, titanium and titanium alloys, and molybdenum and molybdenum alloys, or combinations of such metals and metal alloys, among others.

As demonstrated in various examples, the spatial relationship among the active electrode 14*a*, the insulator 44, and the return electrode 14*b* may adjust the focal point FP of the electric field 40 to effectuate the ablation region AR at the projected distance P. The focal point FP may define a peak current density or center of the ablation region AR. One variable of the spatial relationship among these elements of the electrode assembly 12 is a side profile shape 58 of the active electrode 14*a*. As demonstrated in FIG. 1, the side profile shape 58 is generally recessed away from the distal extent 42 formed by the protruding lip 46 of the rim 48 of the insulator 44. The side profile shape 58 in the depicted example includes a first concave region with a first radius extending over a central portion 60*a* and a second concave region having a second radius extending over a perimeter portion 60*b*. The second radius of the perimeter portion 60*b* of the side profile shape 58 may be larger than the first radius of the central portion 60*a*. In this configuration, the active electrode 14*a* may form a stacked-cup or stacked-bowl configuration that may cause the electric field 40 to be concentrated at the focal point FP, such that the ablation region AR can effectively be applied without the ablation device 10 coming in contact with the target matter or tissue. Additional exemplary profile shapes, geometries, and various aspects of the electrode assembly 12 are discussed in further detail in reference to FIGS. 4-8.

Still referring to FIG. 1, the ablation device 10 may further include one or more aspiration apertures 62, which may be formed through the active electrode 14*a* or the supply electrode. As demonstrated, the aspiration aperture 62 is disposed within the central portion 60*a* of the active electrode 14*a* and is further in connection with a lumen 64 extending through the interior passage 38 formed by the elongated body 18 of the ablation device 10. The lumen 64 may further be in connection with one or more fluid conduits (not shown) in connection with the pump 36 as further discussed in reference to FIG. 12. In operation, fluids may be transferred to/from the ablation region AR via suction or fluid pressure applied to one or more fluid conduits in connection with the lumen 64. Though the aspiration aperture 62 corresponds to a single opening in the example depicted in FIG. 1, various embodiments of the ablation device 10 may include multiple aspiration apertures 62, which may be distributed over the active electrode 14*a* and/or the distal end portion 22 to transfer fluid from/to the ablation region AR.

Figure 4:
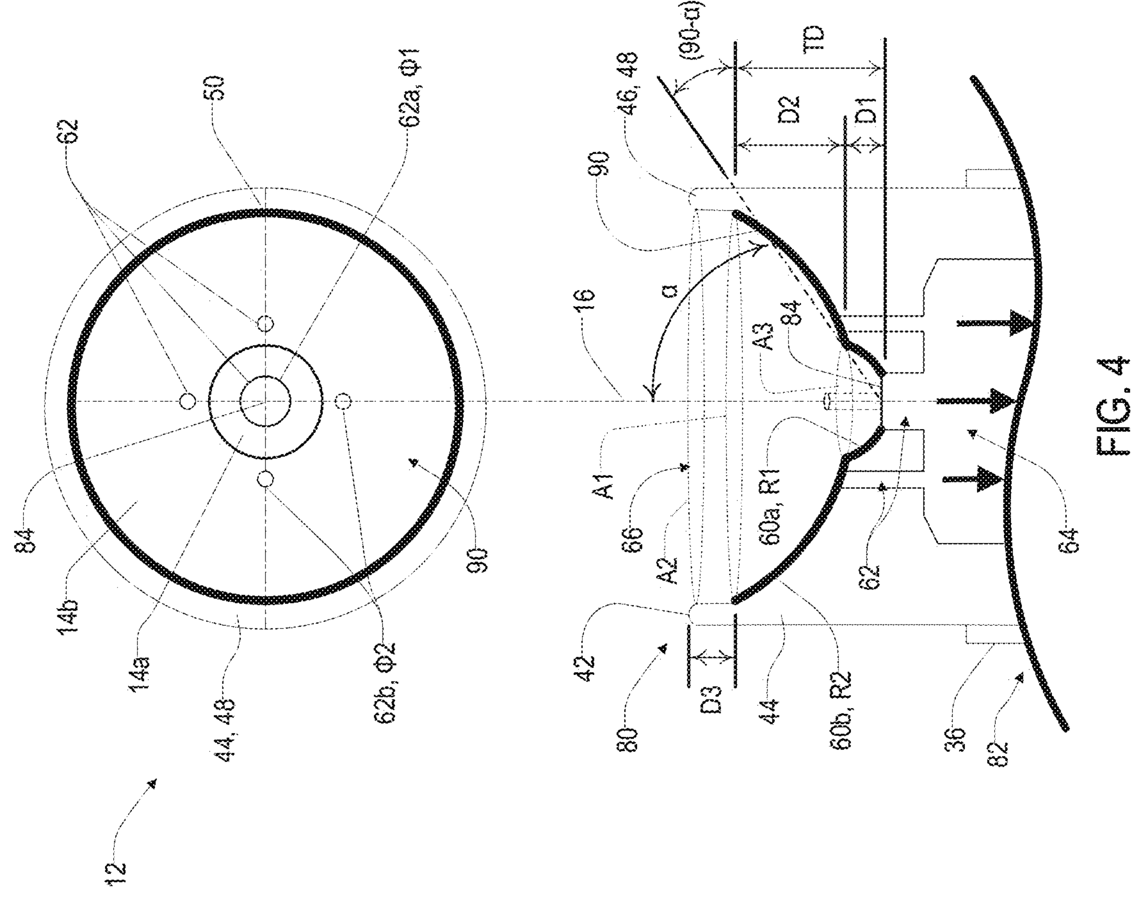
FIG. 4 is an isometric projected view of an electrode assembly of an ablation device.
Figure 5:
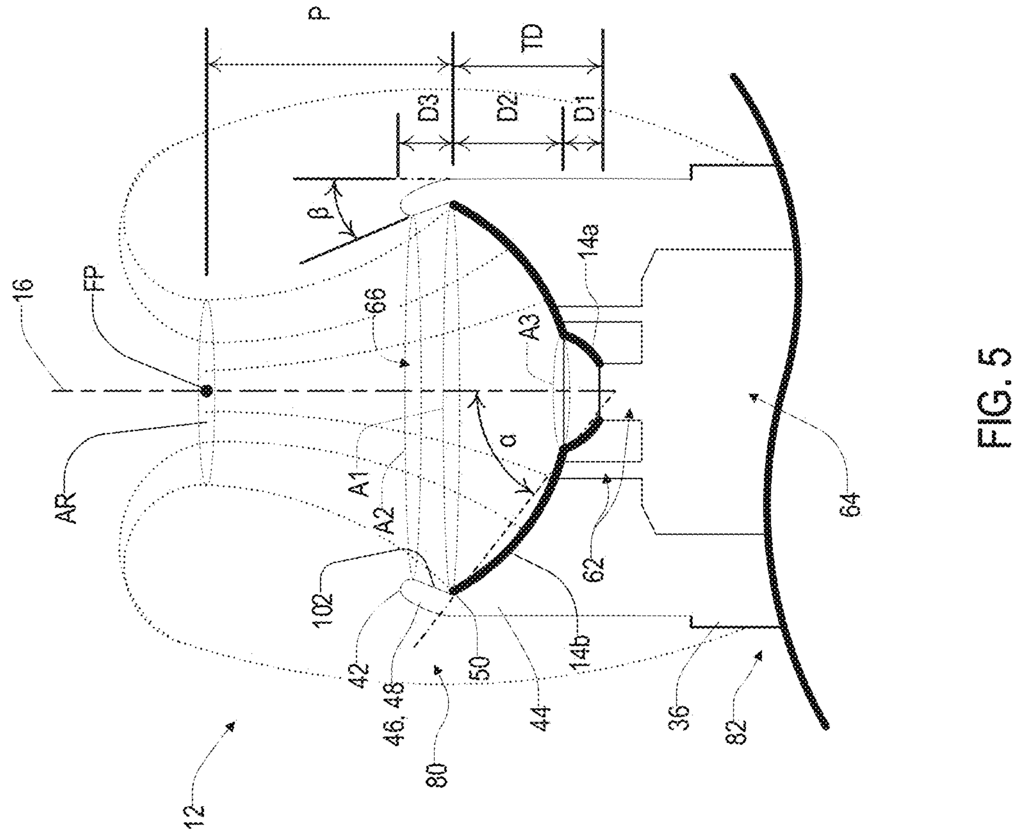
FIG. 5 is a side cross-sectional view of an electrode assembly of an ablation device demonstrating an electric field projected from an active electrode.

Referring now to FIG. 2, the position of the focal point FP and the corresponding current density of the electric field 40 forming the ablation region AR may be adjusted based on the relative surface areas (e.g., A1, A2, A3) of the electrode assembly 12 (also shown in FIGS. 4 and 5). In various examples, the surface areas A1, A2, A3, etc. may be defined by the relative geometries and positions of the features forming the electrode assembly 12. Each of the surface areas may correspond to an opening or space through which the electric field 40 passes. For example, the perimeter 50 and the corresponding portion of the side profile shape 58 of the active electrode 14*a* may define a first area A1 through which the electric field 40 passes. Similarly, an opening 66 formed by the rim 48 of the insulator 44 may define a second area A2 through which the electric field 40 is transmitted to reach the return electrode 14*b*. As later discussed in reference to FIGS. 8A-8C, the spatial relationship among the cross-sectional areas A1, A2, A3, etc. and their relative positions along the projection axis 16 may adjust the focal point FP and the proportions of the ablation region AR. Though discussed in specific examples in reference to the first area A1 and the second area A2, additional features of the electrode assembly 12 may also adjust the projected distance P and proportions of the ablation region AR. For example, the portion of the side profile shape 58 forming the central portion 60*a* of the active electrode 14*a* may define a third surface area A3. Based on the relative position and current density through areas A1, A2, A3, etc., the projected distance P and the proportions of the ablation region AR may be adjusted to suit a variety of applications.

Figure 3:
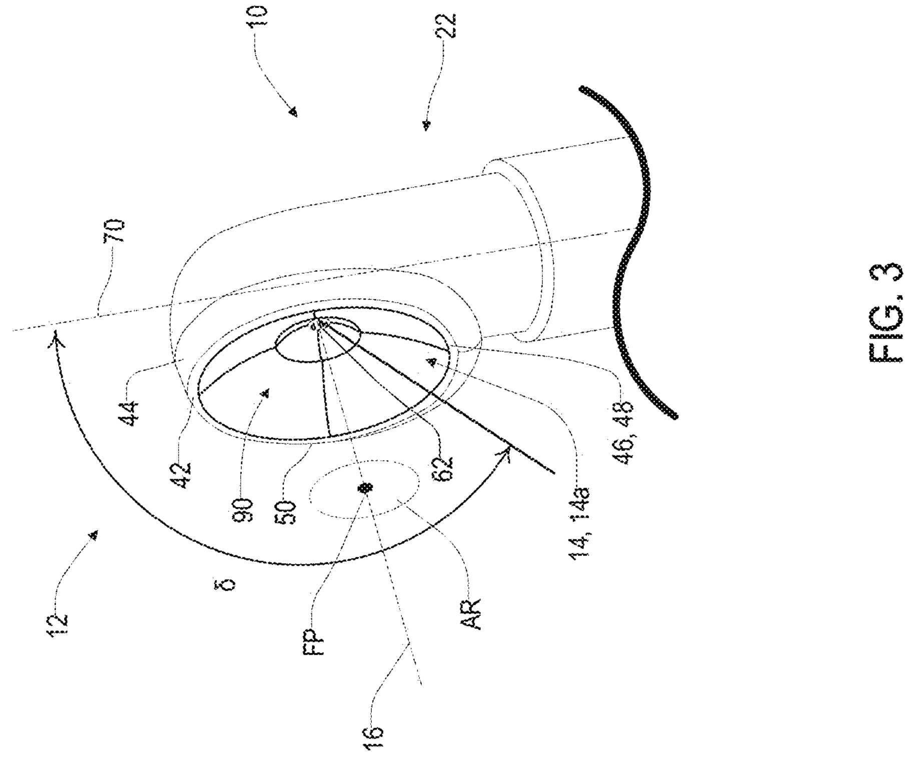
FIG. 3 is a projected view of an ablation device comprising an electrode assembly arranged in a lateral configuration.

Referring now to FIG. 3, the ablation device 10 may incorporate the electrode assembly 12 in various angled geometries. For example, as illustrated in FIG. 1, the projection axis 16 of the electrode assembly 12 may be aligned with a longitudinal axis 70 of the elongated body 18. However, a projection angle δ of the projection axis 16 relative to the longitudinal axis 70 of the elongated body 18 may vary depending on the intended application. As demonstrated in FIG. 3, the projection axis 16 of the electrode assembly 12 is aligned perpendicular to the longitudinal axis 70 in a lateral configuration. In other variations of the ablation device 10, the projection angle δ of the projection axis 16 may vary broadly from approximately 0° to 120° and may only be limited by the clearance space through which the electrode assembly 12 in connection with the elongated body 18 must traverse for an intended procedure. The orientation of the projection axis 16 relative to the elongated body 18 of the ablation device 10 may be adjusted, such that the focal point FP of the ablation region AR may be projected by the electrode assembly 12 to apply ablation treatment for a variety of applications. The remaining elements of the example demonstrated in FIG. 3 are similar to those discussed previously in reference to FIGS. 1 and 2. Accordingly, like reference numerals are designated for like elements in FIG. 3 as well as throughout the detailed description.

Referring now to FIG. 4, isometric projected views of the electrode assembly 12 are shown demonstrating the previously noted features in further detail. The side profile shape 58 of the active electrode may generally be recessed away from the distal extent 42 of the electrode assembly 12 toward the proximal end portion 20. The distal extent 42 may correspond to a point of termination of the electrode assembly 12 and the ablation device 10 and may more generally define a distal end portion 80 of the electrode assembly 12. Opposite the distal end portion 80, a proximal end portion 82 of the electrode assembly 12 may correspond to the portion of the electrode assembly 12 occupied by the return electrode 14*b*. As previously discussed, the side profile shape 58 of the active electrode 14*a* may generally be recessed away from the distal end portion 80 and toward the proximal end portion 82 of the electrode assembly 12. A total distance TD or total depth of the recessed shape, as demonstrated in FIG. 4, is denoted as a combination of a first distance D1 of the central portion 60*a* and a second distance D2 of the perimeter portion 60*b*. As previously discussed, the side profile shape 58 may be formed by a combination of geometries. The example geometry demonstrated in FIG. 4 includes a first rounded concave shape extending over the central portion 60*a* having a first radius R1. The second portion of the side profile shape 58 is formed over the perimeter portion 60*b* by a similarly radially convex shape having a second radius R2.

As previously discussed in FIG. 2, the distances D1, D2, D3 along the projection axis 16 may define the locations of the cross-sectional areas or surface areas A1, A2, A3 through which the electric field 40 passes to effectuate the ablation region AR. More specifically, the first area A1 may be aligned with the perimeter 50 of the active electrode 14*a* or supply electrode. The second area A2 may be defined by the opening 66 of the rim 48 and separated from the first area A1 by a third distance D3 extending along the projection axis 16. The third area A3, as defined in this example by the central portion 60*a* of the active electrode 14*a*, is separated from the first area A1 by the second distance D2 from the perimeter 50 of the active electrode 14*a*. As discussed in reference to various examples, the relative positions and geometries of the active electrode 14*a* and the insulator 44 may be variably positioned along the projection axis 16 to adjust the extent of the projected distance P and/or the proportions of the ablation region AR. In this way, the disclosure may provide for the delivery of current of the electric field 40 to a target region or tissue without the ablation device 10 coming in contact with the tissue.

Based on test results, the projected distance P of the focal point FP of the ablation region may extend beyond the active electrode 14*a* a distance that corresponds to at least twice or two times the total depth TD of the electrode. For example, the projected distance P of the focal point FP may be dependent on the proportions of the electrode assembly 12 as well as the signal supplied to the active electrode and the conditions of the local environment wherein the electric field 40 is induced. Accordingly, for at least one test, the electrode assembly 12 was submerged in a solution of 0.9% saline and the driving signal supplied to the active electrode 14*a* was varied from a minimum setting to a maximum setting with an Arthrex ESU (AR-9800). Accordingly, the maximum power supplied to the active electrode 14*a* from the signal generator of the controller 32 (discussed in reference to FIG. 12) was 575 W with a 218 Ω load. At the maximum setting and a power of the driving signal of approximately 575 W, the projected distance P of the focal point FP was approximately twice the total depth TD (2TD) of the active electrode 14*a*. At a minimum setting of the controller 32, the projected distance P of the focal point FP of the ablation region AR was greater than D3 or just beyond the distal extent 14 of the electrode assembly 12. Accordingly, the electrode assembly 12 provides for projection range of the focal point FP of the ablation region AR that may vary from D3 to the projected distance P of at least two times the total depth TD.

In some embodiments, the side profile shape 58 of the active electrode 14*a* may further define an electrode angle α. As shown, the electrode angle α represents an average angle of the side profile shape 58 of the active electrode 14*a* extending from the intersection of a base 84 of the active electrode 14*a* with the projection axis 16 to the perimeter 50 of the perimeter portion 60*b*. The electrode angle α may indicate an average slope over which the charge of the electric field 40 is conducted and may adjust the projected distance P of the focal point FP of the ablation region AR. For example, adjusting the electrode angle α may adjust the slope (e.g., steeper or shallower) of an emission surface 90 of the active electrode 14*a* and adjust the projected distance P of the focal point FP. Accordingly, the projected distance P may be a function of the electrode angle α. Additionally, while the side profile shape 58 of the active electrode 14*a* may play a role in adjusting the projected distance P, additional features of the electrode assembly 12, for example, the geometry of the insulator 44, may play a complementary role in adjusting projected distance P and the proportions of the ablation region AR.

Referring now FIGS. 4 and 5, a plurality of the aspiration apertures 62 are shown in fluid connection with the lumen 64. Each of the aspiration apertures 62 may pass through a portion of the active electrode 14*a*. The aspiration apertures 62 may be spatially arranged about the active electrode 14*a* or the distal end portion 80, such that a direction of fluid transfer through the aspiration apertures 62 is aligned with the focal point FP or the ablation region AR. The proportions of the aspiration apertures 62 (e.g., relative diameters in the instant example) may vary, such that an intensity of the aspiration may be concentrated at the focal point FP and dissipate gradually from the focal point FP to the boundaries of the ablation region AR. By varying the intensity of the fluid transfer applied via the aspiration apertures 62, the effectiveness of fluid transfer provided by the ablation device 10 may be improved at the projected distance P of the ablation region AR.

For example, a first aspiration aperture 62*a* may extend through the central portion 60*a* (e.g., a center) of the active electrode 14*a* and have a first diameter $\phi$1. Additionally, a plurality of second aspiration apertures 62*b* may be distributed about the active electrode 14*a* (e.g., over the perimeter portion 60*b*) and have a second diameter $\phi$2. The first diameter $\phi$1 may be different than the second diameter $\phi$2. For example, the first diameter $\phi$1 may be larger than the second diameter $\phi$2. In this configuration, the relative fluid transfer via the first aspiration aperture 62*a* may be higher than that associated with each of the second aspiration apertures 62*b*. The relative proportions and distribution of the first and second aspiration apertures 62*a*, 62*b* may adjust the intensity (e.g. volumetric flowrate and velocity) through the apertures 62 and adjust the properties of the fluid transfer from/to the ablation region AR.

A more concrete example of the potential distance of the focal point FP may be understood in reference to a number of working ranges of the second diameter $\phi$2 of the perimeter 50 of the active electrode 14*a*. For example, the diameter $\phi$2 of the perimeter 50 may vary in some applications from approximately 0.5 mm to 10 mm. In implementations wherein the total depth TD is approximately equivalent to a radius of the second diameter $\phi$2, the focal point FP may extend beyond the active electrode 14*a* to a corresponding projection distance of 2 times the total depth TD or two times the radius, which is the distance of the second diameter $\phi$2. Accordingly, the projected distance P of the focal point FP of the ablation region AR may be approximately equal to the second diameter $\phi$2 (e.g., $P \approx \phi 2$). In such examples, the projected distance P may correspond to the diameter $\phi$2 of the perimeter 50 and may vary from approximately 0.5 mm to 10 mm for each of the corresponding diameters $\phi$2 and approximate total depths TD of the electrode assemblies 12. Put differently, the active electrode 14*a* with a second diameter $\phi$2 of 4 mm and a total depth of 2 mm may have a projection distance P of 4 mm beyond the active electrode 14*a*.

As later discussed in reference to FIGS. 6-8, the geometry of the active electrode 14*a* and the electrode assembly 12 may vary broadly. In various cases where a shape of the electrode assembly 12 is not round, the diameters may correspond to widths with corresponding surface areas as denoted by the first area A1. For example, equivalent geometric relationships between the width or average width of the perimeter 50 and the total depth TD of the active electrode 14*a* may provide for similar performance in relation to the effective projected distance P of the focal point FP beyond the active electrode 14*a*. Accordingly, the projected distance of the focal point FP of the ablation region AR may similarly extend beyond the distal extent 42 of the electrode assembly 12.

In some cases, the centrally located first aspiration aperture 62*a* may generally have differing proportions than the radially distributed second aspiration apertures 62*b*. The differing proportions of the first aspiration aperture 62*a* and the second aspiration aperture 62*b* may result in fluid transfer to or from the ablation region AR that varies from the focal point FP to the boundaries of the ablation region AR. Accordingly, the disclosure may further provides for variations in the spatial positions, orientations, and proportions of the aspiration apertures 62 to improve the operation of the ablation device 10. Though discussed in reference to the first diameter $\phi$1 and the second diameter $\phi$2, it shall be understood that the shapes of the aspiration apertures 62 may vary while still maintaining the relative proportions discussed in the example of the first aspiration aperture 62*a* and the second aspiration apertures 62*b*. For example, the distribution of the fluid transfers associated with the aspiration apertures 62 may be adjusted based on their relative proportions of the aspiration apertures 62 and their spatial distribution over the distal end portion 80 of the electrode assembly 12.

As previously discussed in reference to FIG. 2, the second area A2 as defined by an opening 66 formed by the rim 48 of the insulator 44 may be adjusted in combination with other features of the electrode assembly 12 to vary the projected distance P of the focal point FP and proportions of the ablation region AR. Referring now to FIG. 5, the protruding lip 46 that forms the rim 48 is shown having an interior wall 102. The opening 66 formed by the rim 48 may correspond to an electric field aperture that defines a surface area through which the electric field 40 passes as denoted by the second area A2. The protruding lip 46 may generally embody a tab or protrusion that extends from the perimeter 50 of the active electrode 14*a* along the projection axis 16 over a third distance D3. In some implementations, the protruding lip 46 may encircle the perimeter 50 of the active electrode 14*a* and form the rim 48. The protruding lip 46 may extend inward at an aperture angle β along the third distance D3. As demonstrated in the example of FIG. 5, the aperture angle β denotes an angle or slope over which the interior wall 102 may reduce or adjust the proportions of the second area A2 formed by the opening 66 relative to the first area A1 defined by the perimeter 50 of the active electrode 14*a*. Accordingly, the extent of the distance D3 and the magnitude of the aperture angle β may adjust the proportions of the opening 66 or electric field aperture through which the electric field 40 passes.

For example, an increase in the aperture angle β or an increase in the third distance D3 of the protruding lip 46 may reduce or adjust the proportions of the opening 66 as previously denoted by the second area A2 relative to the first area A1. Based on this relationship, the rim 48 formed by the protruding lip 46 may partially enclose the active electrode 14*a* along a portion of the projection distance P extending from the perimeter 50 of the active electrode 14*a* to form the distal end portion 80 of the electrode assembly 12. In this configuration, the interior wall 102 of the rim 48 may gradually decrease the cross-sectional area along the distance D3 relative to the perimeter 50 of the active electrode 14*a*. The reduction of the cross-sectional area (e.g., the electric field aperture) through which the electric field 40 is transmitted may result in a concentration of the current extending beyond the distal extent 42 of the electrode assembly 12, such that the current density is directed to the focal point FP to form the ablation region AR at the projected distance P. Further discussion of the current density and transmission of the electric field 40 through the ablation region AR is provided in reference FIGS. 9A and 9B.

Referring generally to FIGS. 6, 7, and 8, a variety of exemplary geometries of the active electrode 14*a* and the rim 48 formed by the protruding lip 46 are discussed. Though specific examples and variations in geometry are discussed in reference to the exemplary embodiments, it shall be understood that each of the features and shapes of the electrode assembly 12 may be combined to suit specific applications of the ablation device 10. Accordingly, the features set forth in the examples discussed herein may be applied in various combinations.

Figures 6A, 6B, 6C:
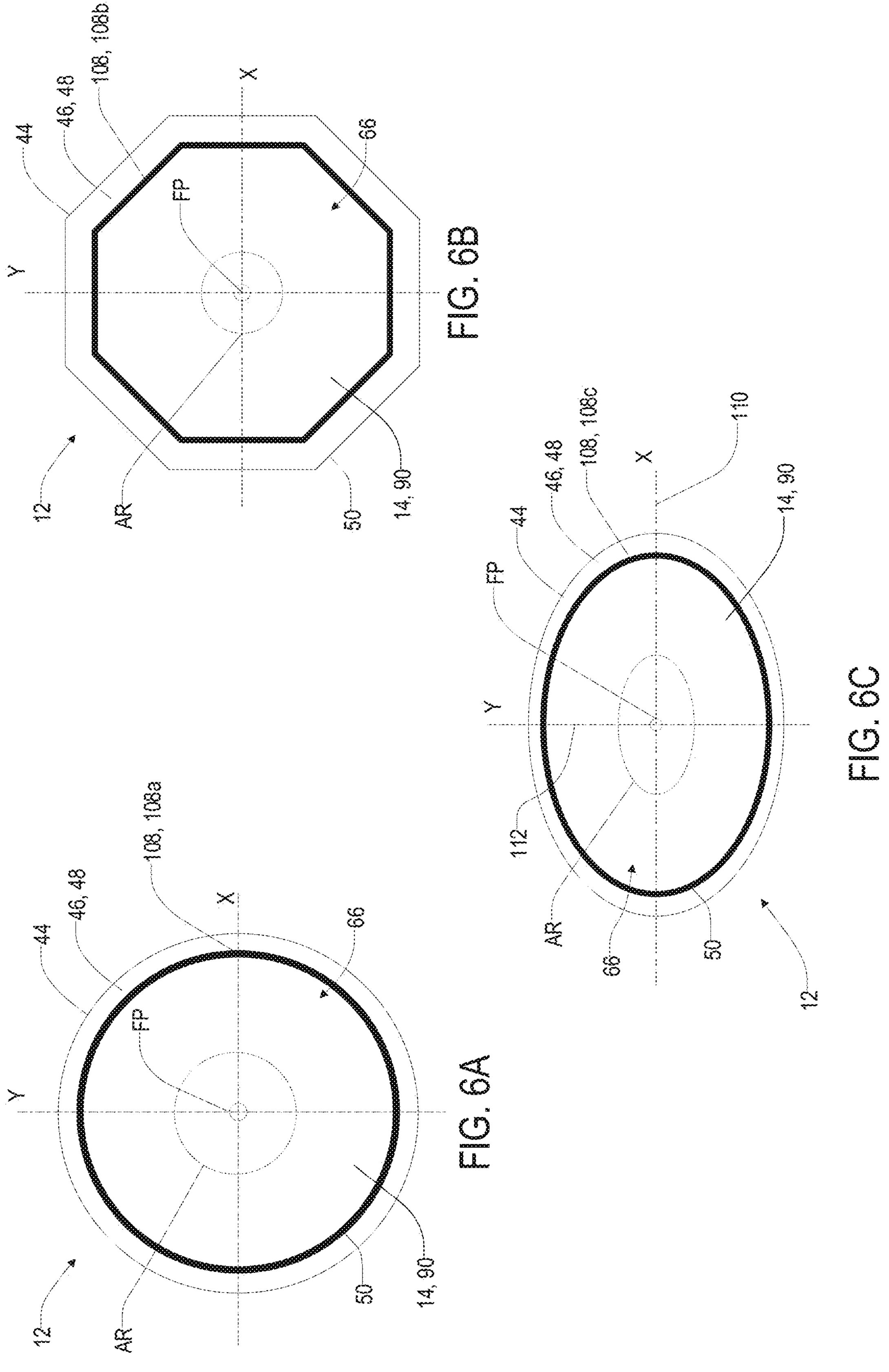
FIG. 6A is a top view of an electrode assembly demonstrating an exemplary geometry of an active electrode.
FIG. 6B is a top view of an electrode assembly demonstrating an exemplary geometry of an active electrode.
FIG. 6C is a top view of an electrode assembly demonstrating an exemplary geometry of an active electrode.

Referring now to FIGS. 6A-6C, top views of examples of the electrode assembly 12 are shown demonstrating various geometries of end profile shapes 108 formed by the active electrode 14*a* and corresponding to the rim 48 of the protruding lip 46. In each of the examples, the focal point FP is shown positioned along the projection axis 16, which may appear to extend directly outward from each of the figures. Additionally, an X-axis is shown splitting upper and lower portions of each of the electrode assemblies 12, and a Y-axis is shown bisecting each of the electrode assemblies 12 into equal side portions. In at least some examples, such as FIGS. 6A, 6B, and 6C, the end profile shape 108 of the active electrodes 14 may be symmetric across two perpendicular axes as demonstrated by the X-axis and the Y-axis.

Referring now to each of the exemplary electrode assemblies 12, FIG. 6A demonstrates a circular end profile 108*a*; FIG. 6B demonstrates an octagonal end profile 108*b*; and FIG. 6C demonstrates an elliptical end profile 108*c*. Though FIG. 6B specifically refers to an octagonal shape for the electrode assembly 12, the shape may correspond to nearly any enclosed polygon or geometric shape, including, but not limited to, triangles, squares, pentagons, hexagons, etc. The electrode assemblies 12 demonstrated in FIGS. 6A and 6B are shown generating circular ablation regions AR. In contrast, the elongated elliptical end profile 108*c* demonstrated in FIG. 6C may produce an elongated ablation region AR. As shown, the ablation region AR of the elliptical end profile 108*c* is greater in proportion along a major axis 110 than a proportion extending along a minor axis 112 of the elliptical end profile 108*c*. Accordingly, implementations of the electrode assembly 12 with end profile shapes 108 with uneven proportions along the X- and Y-axes, similar to the ellipse demonstrated in FIG. 6, may provide for similarly elongated ablation regions AR. Adjusting the proportions of the ablation region AR may be beneficial to target tissue having differing proportions for ablation procedures. Other similarly elongated geometric shapes (e.g., rectangles or octagons elongated along the X-axis, etc.) may provide for similarly elongated ablation regions AR.

Referring now to FIGS. 7A-7C, side profile views of exemplary electrode assemblies 12 are shown demonstrating various examples of side profile shapes 58. Each of the examples of FIG. 7A-7C may include continuous profile shapes extending along the total depth or total distance TD of the active electrode 14*a*. As shown in FIG. 7A, a round profile shape 58*a* extends along a consistent radius forming the recessed emission surface 90. As demonstrated in FIG. 7B, the active electrode 14*a* has a linear profile shape 58*b*, which may form triangular shape or a conical bowl shape. FIG. 7C demonstrates the active electrode 14*a* having an elliptical profile shape 58*c*. Each of the side profile shapes 58 may adjust the focal point FP of the current density of the electric field 40 to adjust the projected distance P of the ablation region AR.

Additionally, each of the examples of FIGS. 7A-7C demonstrate of variations the distance D3 or length of the protruding lip 46 forming the rim 48 of the insulator 44, as previously discussed. Each of the examples demonstrates the interior wall 102 with an aperture angle β of zero, such that the first area A1 is approximately equal to the second area A2. The extension of the protruding lip 46 may also change or adjust the distribution or range of the electric field 40. Accordingly, the projected distance P of the focal point FP and the proportions of the ablation region AR may also be a function of the proportions of the protruding lip 46 forming the rim 48 as further discussed in reference to FIGS. 8A-8C.

Referring now to FIGS. 8A, 8B, and 8C, examples of side profile shapes 58 of the electrode assembly 12 are demonstrated with more complex geometry than those previously illustrated in FIGS. 7A-7C. By varying the features and proportions of the side profile shape 58 and/or the rim 48 of the insulator 44, the electric field 40 maybe be tuned to adjust a current density and distribution of energy passing through the ablation region AR. Referring now to FIG. 8A, the side profile shape 58 comprises a round profile shape 58*a* along the perimeter portion 60*b* and a linear profile shape 58*b* along the central portion 60*a*. In this configuration, the active electrode 14*a* may form a concaved dome shape over the perimeter portion 60*b* and a conical bowl shape over the central portion 60*a*. The rounded profile shape 58*a* may extend over the second distance D2 and the linear profile shape 58*b* may extend along the first distance D1.

Still referring to FIG. 8A, the protruding lip 46 extends over the third distance D3 from the perimeter 50 of the active electrode 14*a*. The interior wall 102 includes a vertical portion 120 extending from the perimeter 50 and an arched portion 122 that extends radially inward toward the projection axis 16. In this configuration, the rim 48 may form a partial enclosure 124 reducing the proportions of the opening 66 formed by the rim 48 relative to the proportions of the perimeter 50 of the active electrode 14*a*. Accordingly, the example of the electrode assembly 12 demonstrated in FIG. 8A provides for the second area A2 to be reduced relative to the first area A1. In this configuration, the electric field 40 that passes through the opening 66 or electric field aperture may be concentrated, such that the focal point FP of the ablation region AR is extended outward from the distal extent 42 of the electrode assembly 12 to the projected distance P. Finally, the transition between the central portion 60*a* and the perimeter portion 60*b* of the side profile shape 58 may result in variations in the current density of the electric field 40 passing through the third area A3.

As demonstrated in FIG. 8B, the active electrode 14*a* may include multiple variations of the rounded profile shape 58*a* forming the central portion 60*a* as well as the perimeter portion 60*b*. The second radius R2 of the perimeter portion 60*b* is different than the first radius R1 of the central portion 60*a*. In some embodiments, the second radius R2 of the perimeter portion 60*b* may be greater than the first radius R1 of the central portion 60*a*. In the example shown, the distance or depth of the perimeter portion 60*b* extends along the second distance D2 and the central portion 60*a* extends over the first distance D1. As shown, depth of the active electrode 14*a* is the combination of the first distance D1 and the second distance D2, denoted as the total depth or distance TD.

Still referring to FIG. 8B, the protruding lip 46 is shown extending from the perimeter 50 of the active electrode 14*a* over the third distance D3. The interior wall 102 is angled inward from the perimeter 50 toward the projection axis 16 over the average aperture angle β. The interior wall 102 demonstrated in FIG. 8B slopes inward along the third distance D3 and forms a curved profile having a third radius R3. In this configuration, the second area A2 formed by the opening 66 or electric field aperture of the rim 48 is decreased relative to the first area A1 as defined by the perimeter 50 of the active electrode 14*a*. As shown, the second area A2 of the opening 66 may decrease in proportions at an increasing rate (e.g. along a parabolic curve) over the third distance D3 from the perimeter 50. Additionally, the third area A3, as defined by the transition between the perimeter portion 60*b* and the central portion 60*a* of the side profile shape 58, further defines the third area A3 that may adjust the distribution of the electric field 40, such that the ablation region AR may be projected to the focal point FP at the projected distance P.

Referring now to FIG. 8C, the side profile shape 58 differs from that demonstrated in FIG. 8B in that the rounded portions are joined by an intermediate curve 126 that provides for a splined transition between the first radius R1 and the second radius R2. Additionally, the interior wall 102 of the protruding lip 46 extends linearly along the aperture angle β. As a result of the inward sloping interior wall 102 formed by the protruding lip 46 of the rim 48, the opening 66 or electric field aperture formed through the insulator 44 is diminished or decreased relative to the perimeter 50 of the active electrode 14*a*. Accordingly, the second area A2 is linearly decreased relative to the first area A1 over the third distance D3. The splined geometry provided by the intermediate curve 126 of the side profile shape 58 in the example of FIG. 8C may further adjust the distribution of the electric field 40 produced by the electrode assembly 12.

Figure 9B:
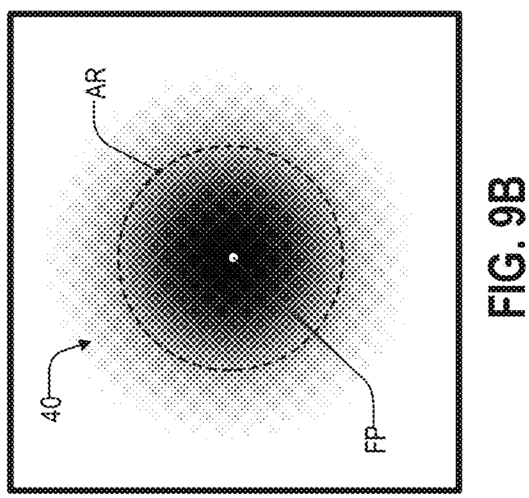
FIG. 9B is graphical representation an ablation region generated by an electrode assembly.
Figure 9A:
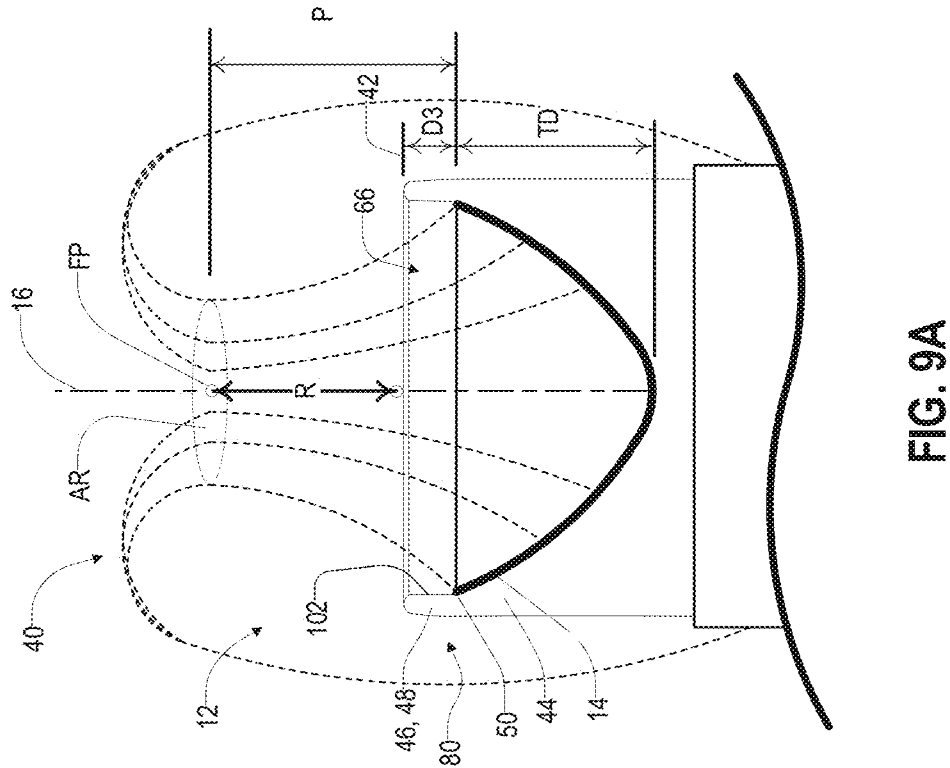
FIG. 9A is a side view of an electrode assembly demonstrating a representation of an electric field forming an ablation region at a focal point projected beyond a distal extent of an ablation device.

Referring now to FIGS. 9A and 9B, an example of the electric field 40 formed by the electrode assembly 12 is shown. FIG. 9A demonstrates a side profile view of the electric field 40, and FIG. 9B demonstrates the distribution of the current density over the ablation region AR formed by the ablation device 10. As discussed in reference to various preceding examples, the geometry of the electrode assembly 12 may adjust the concentration and distribution of the electric field 40, such that the focal point FP of the ablation region AR is extended beyond the distal extent 42 of the electrode assembly 12 over the projected distance P. The projected distance P of the ablation region AR may be defined based on a current density that may be required to effectuate an ablation procedure. As previously discussed, the focal point FP may define a peak current density or center of the ablation region AR. Similarly, the current density may be measured as an average over the ablation region AR. For example, the proportions of the ablation region AR and the extents of the corresponding surface may be defined as an area that receives an average current density of the electric field 40 sufficient to effectuate heating of target tissue. In some examples, the current density may increase closer to the focal point FP of the ablation region AR and diminish near a perimeter of the ablation region AR. However, the effectiveness of the ablation area AR at the projected distance may account for such variations to determine the effectiveness of the ablation region as an average current density over the planar region or surface area forming the ablation region AR.

As previously discussed, in a controlled environment, the electrode assembly 12 was submerged in a solution of 0.9% saline and the driving signal supplied to the active electrode 14*a* was varied from a minimum setting to a maximum setting with an Arthrex ESU (AR-9800). Accordingly, the maximum power supplied to the active electrode 14*a* from the signal generator of the controller 32 was 575 W with a 218 Ω load. At the maximum setting and a power of the driving signal of approximately 575 W, the projected distance P of the focal point FP was approximately twice the total depth TD (2TD) of the actively electrode 14*a*. At a minimum setting of the controller 32, the projected distance P of the focal point FP of the ablation region AR was greater than D3 or just beyond the distal extent 14 of the electrode assembly 12. Accordingly, the electrode assembly 12 provides for projection range R of the focal point FP of the ablation region AR that may vary from D3 to the projected distance P of at least two times the total depth TD.

Figure 10:
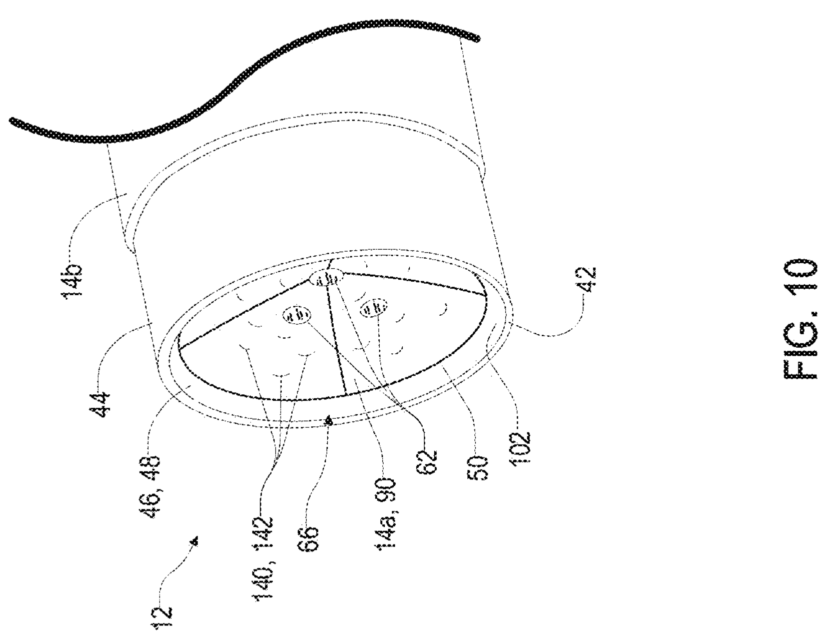
FIG. 10 is an exemplary projected view of an electrode assembly incorporating a plurality of surface features.

FIG. 10 demonstrates a projected view of another exemplary electrode assembly 12 of the ablation device 10. As shown, a plurality of the aspiration apertures 62 are formed through the active electrode 14*a*. Additionally, surface features 140 are distributed over the emission surface 90 of the active electrode 14*a*. The surface features 140 may correspond to convex bumps 142 or concave grooves formed over the emission surface 90. The proportions, frequency, and spatial distribution of the surface features 140 over the emission surface 90 may further be adjusted to control the distribution and concentration of the electric field 40. Accordingly, the surface features 140 may be incorporated in various exemplary embodiments of the electrode assembly 12 based on the particular specifications of a desired application.

Figure 11B:
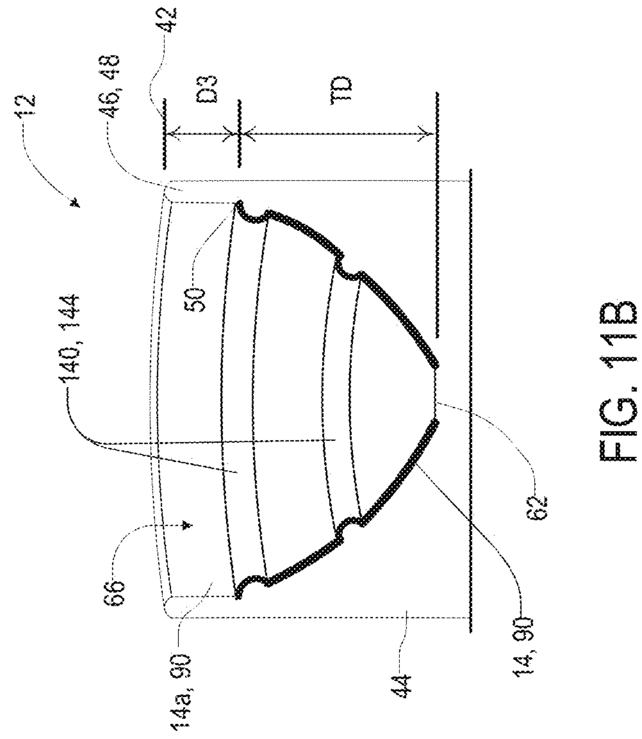
FIG. 11B is an exemplary side cross-sectional view of the electrode assembly depicted in FIG. 11A.
Figure 11A:
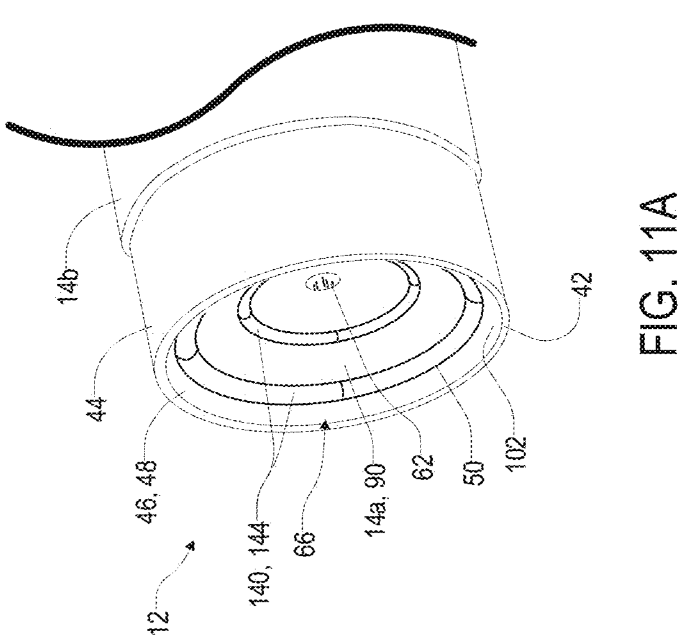
FIG. 11A is an exemplary projected view of an electrode assembly incorporating a plurality of surface features.

FIGS. 11A and 11B demonstrate an additional example of an electrode assembly incorporating a plurality of surface features 140. As shown, the surface features 140 may correspond to one or more raised ridges 144, bumps, or undulations that extend circumferentially about the emission surface 90 at one or more angles or latitudes. As discussed herein, the term latitude may correspond to a perimeter line, similar or equivalent to a latitudinal perimeter line of a sphere, extending about the emission surface 90 at a depth positioned along the total depth TD of the active electrode 14*a*. In this configuration, the one or more ridges 144 may extend as annular or ring-shaped ridges extending inward or outward from the emission surface 90. As depicted, the ridges 144 extend outward from the emission surface 90, but the surface features may also form annular grooves or indentations in the emission surface 90. The raised ridges 144 and grooves (not shown) may also alternate or be incorporated over the emission surface 90 in various combinations with the convex bumps 142 or concave grooves as previously discussed in reference to FIG. 10.

Figure 12:
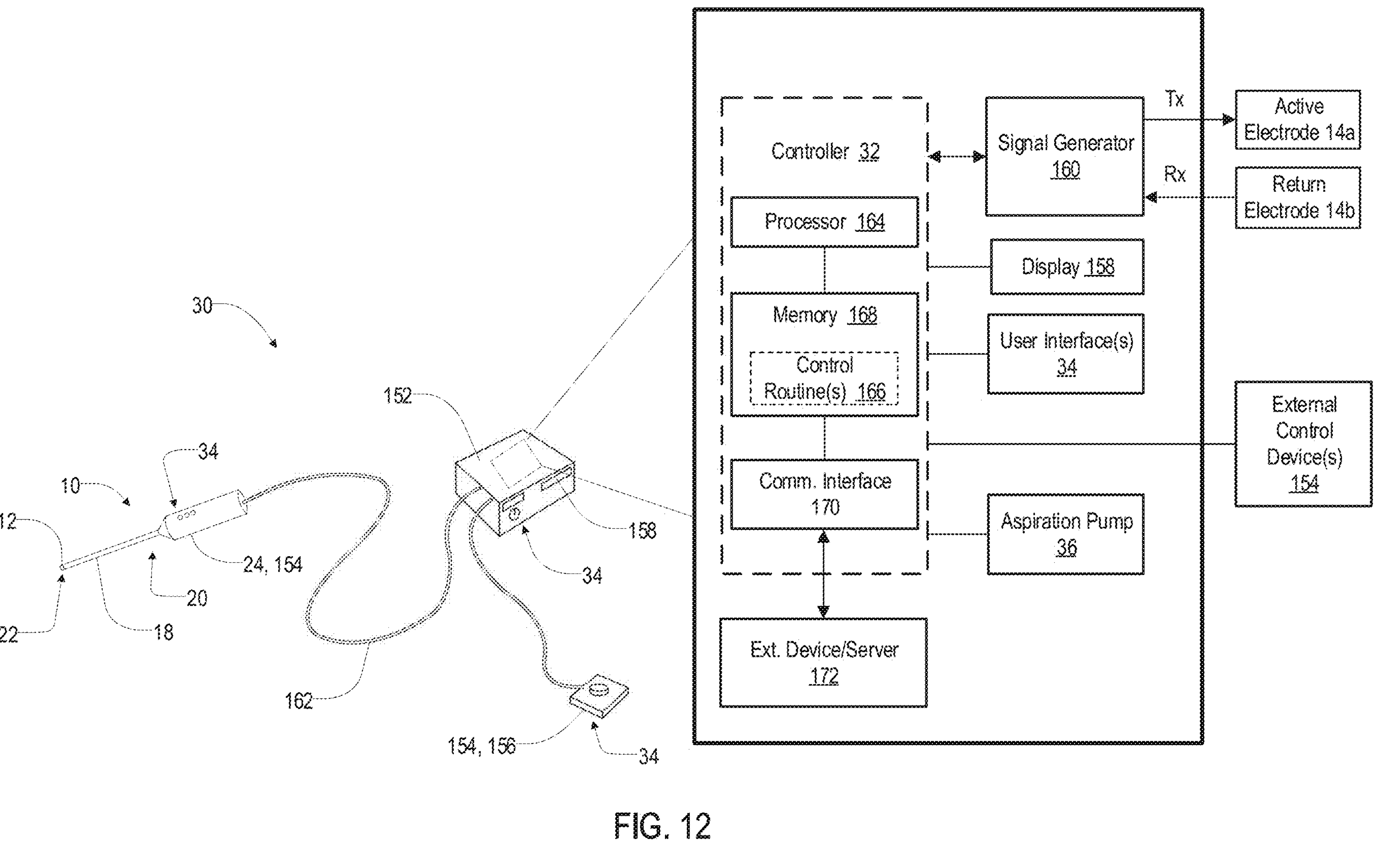
FIG. 12 is an illustrative diagram of an electro-surgical ablation system including a block diagram of a controller of an ablation system.

Referring now to FIG. 12, the ablation system 30, as previously referenced in FIG. 1, is shown demonstrating the controller 32 and the pump 36 or aspiration pump. In operation, the controller 32 may receive inputs via the user interface 34, which may be distributed among a control unit 152 as well as one or more external control devices 154. The external control devices 154 may correspond to one or more electronic or electromechanical buttons, triggers, or pedals incorporated on the handle portion 24 grip of the ablation device 10, one or more foot pedals 156, and additional peripherals and devices communicatively connected to the control unit 152. The user interface 34 may include one or more switches, buttons, dials, and/or displays, which may include soft-key or touchscreen devices incorporated in a display device 158 (e.g., liquid crystal display [LCD], light emitting diode [LED] display, cathode ray tube [CRT], etc.). In response to inputs received from the user interface 34, the controller 32 may activate or adjusts the settings of the control signals communicated to the electrode assembly 12. The control signals generated by control unit 152 may be controlled by a signal generator 160 configured to generate the AC or RF signals that activate the electric field 40 in response to control instructions (e.g., timing signals, amplification, etc.) communicated from the controller 32. The control signals may be communicated from the signal generator 160 of the control unit 152 to the ablation device 10 via one or more conductive connectors 162.

The conductive connectors 162 may be connected to the active electrode 14*a* to transmit the output control signal Tx and connected to the return electrode 14*b* to receive a return signal Rx. The return signal Rx may be monitored by the controller 32 to provide closed-loop feedback to adjust the control signal Tx. The control signal Tx from the signal generator 160 may correspond to an AC driving signal generated in response to time-modulated signals from a processor 164 of the controller 32. The AC driving signal may induce the electric field 40 in the form of RF energy. The modes of operation of the ablation device 10 may be controlled by adjusting the amplitude of the voltage and timing of the signal modulation that controls the signal generator 160 to generate RF frequency signals. Accordingly, by adjusting the voltage potential and the frequency or timing characteristics of the AC driving signal output from the signal generator 160, the controller 32 may control the operation of the ablation device 10 in response to inputs received via the user interface 34. In some embodiments, the controller 32 may be configured to activate one or more preset modes (e.g. ablation, coagulation) and the associated power levels or frequencies as presets in response to inputs received from the user interface 34.

The performance or specifications of the control unit 152 (e.g. power supply, heat dissipation, peak control frequency, etc.) may be designed to accommodate the target properties of the control signals Tx or RF frequency signals communicated to the ablation device 10. In general the frequency of the control signal Tx communicated to the active electrode 14*a* may vary from approximately 10 kHz to 1 MHz and may vary from approximately 50 kHz to 500 kHz. Additionally, the equivalent constant direct current voltage used to generate the control signal Tx from the signal generator 160 may range from approximately 5V to 500V. Sample test data reported for this disclosure was generated using maximum power settings of an Arthrex ESU (AR-9800) signal generator. For example, the maximum power supplied to the active electrode 14*a* from the signal generator was 575 W with a 218 Ω load.

The processor 164 of the controller 32 may be implemented as a microprocessor, microcontroller, application-specific integrated circuit (ASIC), or other circuitry configured to perform instructions, computations, and control various input/output signals to control the ablation system 30. The instructions and/or control routines 166 of the system 30 may be accessed by the processor 164 via a memory 168. The memory 168 may comprise random access memory (RAM), read only memory (ROM), flash memory, hard disk storage, solid state drive memory, etc. The controller 32 may incorporate additional communication circuits or input/output circuitry represented in FIG. 12 as a communication interface 170. In an exemplary embodiment, the communication interface 170 or more generally the controller 32, may include digital-to-analog converters, analog-to-digital converters, digital inputs and outputs, as well as one or more peripheral communication interfaces or busses. The peripheral communication interfaces of the communication interface 170 may be implemented with by various communication protocols, such as serial communication (e.g., CAN bus, I2C, etc.), parallel communication, network communication (e.g., RS232, RS485, Ethernet), wireless network communication (Wi-Fi, 802.11, etc.). In some examples, the controller 32 may be in communication with one or more external devices 172 (e.g., control devices, peripherals, servers, etc.) via the communication interface 170. Accordingly, the control unit 152 may provide for communication with various devices to update, maintain, and control the operation of the ablation system 30.

Though not illustrated in the figures, the pump 36 or aspiration pump may be connected via one or more fluid conduits that may pass through the handle portion 24 and connect to the lumen 64 to effectuate fluid transfer via the aspiration aperture(s) 62. The pump 36 may be controlled via the user interface 34 of the controller 32 to adjust a flow rate or intensity of the fluid transfer. The pump 36 may be implemented with a variety of pumping technologies (e.g., peristaltic, reciprocating, etc.) and may vary in fluid transfer capacity based on the application of the ablation device 10.

The various examples of the electrode assembly 12 of the ablation device 10 provide for a variety of features and assemblies that may adjust a distribution of the electric field 40. In some embodiments, the adjustment of the distribution of the electric field 40 may result in the ablation region AR to be adjusted beyond a distal end portion 80 of the electrode assembly to a projected distance P of the focal point FP. In this way, the disclosure may provide for the ablation device 10 to apply an ablation treatment without the ablation device 10 or any portion of the electrode assembly 12 coming in contact with tissue targeted for treatment. The projection of the ablation region AR and the resulting non-contact surgical procedures may improve the visibility of the targeted tissue and the ability of the ablation device 10 to apply therapy at distances extending into the targeted tissue at depths controlled by the projected distance P of the focal point FP of the ablation region AR.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents

What is claimed:

1. An electrode assembly for a surgical ablator, the electrode assembly comprising:

an insulator comprising a distal end portion and a proximal end portion, the insulator comprising a rim forming a distal extent of the distal end portion, the rim forming an aperture disposed in the distal end portion;

a supply electrode disposed in the aperture and forming a cavity having a profile shape recessed from the distal end portion toward the proximal end portion, wherein the profile shape forms an inner contour of the supply electrode having a first radius and an outer contour enclosing the inner contour having a second radius different from the first radius; and wherein the electrode assembly is configured to project a focal point of an ablation region emitted from the supply electrode through the aperture to a projection distance beyond the distal extent.

2. The electrode assembly according to claim 1, wherein a projection axis extends centrally from the supply electrode through the focal point and the profile shape forms an electrode angle relative to the projection axis, wherein the projection distance of the focal point is a function of the electrode angle.

3. The electrode assembly according to claim 2, wherein the profile shape extends along a varying slope that changes from a central portion of the supply electrode to a perimeter of the supply electrode, wherein the electrode angle is an average of the varying slope of the profile shape.

4. The electrode assembly according to claim 1, wherein the profile shape of the supply electrode forms a depth (D) of the aperture and the projection distance extends to a distance of two times the depth (2D) from the distal end portion of the supply electrode.

5. The electrode assembly according to claim 1, wherein the rim forms an interior wall of the aperture that extends a first distance from the supply electrode to the distal extent.

6. The electrode assembly according to claim 5, wherein the first distance is between 5% of the depth D (0.05D) to 100% of the depth D.

7. The electrode assembly according to claim 5, wherein the interior wall defines a cross section of the aperture formed by the rim, wherein the cross section decreases at an aperture angle along the first distance from the supply electrode to the distal extent.

8. The electrode assembly according to claim 7, wherein the cross section decreases at an increasing rate along at least a portion of the first distance.

9. The electrode assembly according to claim 5, wherein the supply electrode forms a perimeter defining a first area and the aperture of the rim forms an opening proximate to the distal extent defining a second area, wherein the first area is greater than the second area.

10. The electrode assembly according to claim 1, wherein the focal point is projected along a projection axis from a central portion of the supply electrode through the aperture of the rim to the projection distance.

11. The electrode assembly according to claim 1, wherein the profile shape of the cavity extends from a perimeter of the supply electrode to a base of a central portion of the supply electrode over a depth ranging from 0.25 mm to 10 mm.

12. The electrode assembly according to claim 1, wherein the profile shape comprises a rounded concave shape.

13. The electrode assembly according to claim 1, wherein the first radius is smaller than the second radius.

14. The electrode assembly according to claim 1, further comprising:

a return electrode conductively separated from the supply electrode via the insulator and disposed adjacent to the proximal end portion.

15. The electrode assembly according to claim 1, wherein the inner contour and the outer contour form a stacked configuration.

16. A surgical ablation system comprising:

an electrode assembly comprising a proximal end portion and a distal end portion, the electrode assembly comprising:

an insulator comprising a rim forming a distal extent of the distal end portion, the rim forming an aperture disposed in the distal end portion; and a supply electrode disposed in the aperture and forming a cavity having a profile shape recessed from the distal end portion toward the proximal end portion, wherein the electrode assembly is configured to project a focal point of an ablation region along a projection direction, and the projection direction extends from the supply electrode through the aperture of the rim to a projection distance beyond the distal extent, wherein the profile shape forms an inner contour of the supply electrode having a first surface area, an outer contour enclosing the inner contour, the outer contour having a second surface area larger than the first surface area, and a transition section distinguishing the inner contour and the outer contour; and a controller comprising a signal generator and a processor, wherein the controller is configured to control a radio frequency (RF) signal conducted to the supply electrode, wherein the supply electrode is configured to transmit RF energy to the focal point of the ablation region in response to the RF signal.

17. The ablation system according to claim 16, wherein the ablation region is defined perpendicular to the projection direction.

18. A surgical ablation apparatus comprising:

an insulator comprising a proximal end portion and a distal end portion extending along a longitudinal axis, the insulator comprising a rim forming an aperture disposed in the distal end portion;

a supply electrode disposed in the aperture and forming a cavity having a profile shape recessed from the distal end portion toward the proximal end portion, wherein the supply electrode is configured to project a focal point of an ablation region along a projection direction that extends from the supply electrode through the aperture of the rim to a projection distance beyond the distal end portion, wherein the profile shape of the supply electrode forms a first concave region and a second concave region enclosing the first concave region about the longitudinal axis, where the second concave region is distinguishable from the first concave region; and at least one aspiration aperture extending through the supply electrode to a lumen, wherein the at least one aspiration aperture is aligned with the focal point.

19. The ablation apparatus according to claim 18, wherein the at least one aspiration aperture comprises a plurality of aspiration apertures formed through the supply electrode, wherein the plurality of aspiration apertures are aligned with the focal point over the profile shape of the supply electrode.

20. The ablation apparatus according to claim 18, wherein the second concave region is larger than the first concave region.

21. The ablation apparatus according to claim 18, wherein the at least one aspiration aperture extends through the second concave region.

22. The ablation apparatus according to claim 18, wherein the at least one aspiration aperture comprises a first aspiration aperture extending through the first concave region and a second aspiration aperture extending through the first concave region.

23. The ablation apparatus according to claim 18, wherein the first concave region and the second concave region form a stacked-bowl configuration.

* * * * *